United States Patent [19]

Wünsch

[11] 4,167,508

[45] Sep. 11, 1979

[54] PHLORETHYL-β-ALANYL-SECRETINE

[75] Inventor: Erich Wünsch, Tutzing, Fed. Rep. of Germany

[73] Assignee: Max-Planch-Gesellschaft zur Forderung der Wissenschaften, Gottingen, Fed. Rep. of Germany

[21] Appl. No.: 807,533

[22] Filed: Jun. 17, 1977

[30] Foreign Application Priority Data

Jun. 23, 1976 [DE] Fed. Rep. of Germany ....... 2627988

[51] Int. Cl.² .................. C07C 103/52; C07G 7/00; A61K 37/100
[52] U.S. Cl. .............................. 260/112.5 R; 424/177
[58] Field of Search .................. 260/112.5 R; 424/177

[56] References Cited

U.S. PATENT DOCUMENTS

| | | | |
|---|---|---|---|
| 3,740,385 | 6/1973 | Ondetti | 260/112.5 R |
| 3,987,014 | 10/1976 | Giducci et al. | 260/112.5 R |

FOREIGN PATENT DOCUMENTS 2500579  7/1975  Fed. Rep. of Germany .... 260/112.5 R

OTHER PUBLICATIONS

Chem. Abs., vol. 79 (1973), 134106d.

*Primary Examiner*—Delbert R. Phillips
*Assistant Examiner*—Blondel Hazel
*Attorney, Agent, or Firm*—Fisher, Christen & Sabol

[57] ABSTRACT

A radioiodinated phloretyl-β-alanyl-secretin, its salts and its protected derivatives. A process for the manufacture of a radioiodinated phloretyl-β-alanyl-secretin and/or a salt thereof which process involves reacting phloretyl-β-alanyl-secretin and/or a salt thereof with radioactive iodine. Phloretyl-α-alanyl-secretin, its salts and its protected derivatives. A method for the determination of secretin in a sample, which involves; mixing the sample with a known amount of a radioiodinated phloretyl-β-alanyl-secretin and an antibody specific for secretin; measuring the degree of binding of the labelled radioiodinated phloretyl-β-alanyl-secretin; and determining the amount of secretin present in the sample by comparing the degree of binding with a standard curve which has been obtained by adding known amounts of secretin to a defined mixture of the radioiodinated phloretyl-β-alanyl-secretin and the antibody and determining the degree of binding for this known amount of secretin.

3 Claims, No Drawings

PHLORETHYL-β-ALANYL-SECRETINE

BACKGROUND OF THE INVENTION

1. Field of the Invention

The present invention relates to the determination of secretin. More particularly, the invention is concerned with a novel radioiodinated secretin derivative and a process for the manufacture thereof. The invention is also concerned with the use of said derivative in the biological determination of secretin. Further, the invention is concerned with novel intermediates useful in the manufacture of said derivative.

2. Prior Art

Although secretin is a peptide which has been known for a long time, it has hitherto not been possible to make firm statements concerning its physiological role in the digestive process.

In particular, the establishment of a radioimmunological determination test for secretin has been found to be problematical since the secretin molecule lacks a tyrosyl group as the binding site for radioactive iodine.

It is, however, possible to iodinate the histidyl group at the NH$_2$ end of the secretin molecule, but the labelling process has been found to be less suitable (see Hunter, "Handbook of Experimental Immunology", pp. 600–665, 1967).

As disclosed in German Offenlegungsschrift No. 2500579, an attempt has also been made to synthesize a tyrosine-containing secretin derivative. This secretin derivative, in which the phenylalanine group normally present in the 6-position is replaced by the tyrosine group, leads, however, to a radioiodinated secretin ($^{125}$I-6-Tyr-secretin) having a distinctly reduced immunoreactivity in comparison with normal secretin (see Biochem. Biophys. Res. Comm. 64, 1036–1040, 1965).

DESCRIPTION OF THIS INVENTION

The present invention now provides a novel radioiodinated secretin derivative which does not possess the aforementioned disadvantages and which is superior as a "tracer" to the labelled normal secretin.

More particularly, the present invention provides a radioiodinated phloretyl-β-alanyl-secretin, its salts thereof and its protected derivatives, the term "phloretyl" used herein denoting the 3-(4-hydroxy-phenyl)-propanyl group.

Especially preferred radioiodinated derivatives of phloretyl-β-alanyl-secretin are:

N-[3-(4-hydroxy-3-$^{125}$I-phenyl)-propanoyl]-β-alanyl-secretin and

N-[3-(4-hydroxy-3,5-di$^{125}$I-phenyl)-propanoyl]-β-alanyl-secretin.

Further, the present invention is concerned with phloretyl-β-alanyl-secretin, which is useful as an intermediate for the manufacture of the aforementioned radioiodinated derivatives, its salts and its protected derivatives.

As used in this specification, the term "salts" includes the salts which are customary in peptide chemistry, such as, salts with inorganic acids (e.g., hydrochloric acid, hydrobromic acid, phosphoric acid, sulphuric acid, perchloric acid and the like) and with organic acids (e.g., acetic acid, oxalic acid, maleic acid, malic acid, tartaric acid, citric acid and the like).

The term "protected derivative" includes the derivatives which carry the protecting groups which are customary in peptide chemistry.

Examples of amino protecting groups are those of the acyl type (e.g., formyl, phthalyl, trifluoroacetyl, p-tosyl, aryl- and alkylphosphoryl, phenyl- and benzylsulphonyl, tritylsulphenyl, o-nitrophenylsulphenyl, γ-chlorobutyryl and o-nitrophenoxyacetyl), of the alkyl type (e.g., trityl, benzyl and alkylidene) or of the urethane type [e.g., carbobenzoxy, p-bromo-, p-chloro- or p-methoxycarbobenzoxy, tolyloxy-, allyloxy-, cyclopentyloxy-, cyclohexyloxy-, t.butoxy- or 1,1-dimethylpropoxy-, 2-(p-biphenylyl)-2-propoxy-carbonyl, benzylthiocarbonyl and 1-adamantyloxycarbonyl], etc.

Examples of amide protecting groups are xanthenyl, 2,4-dimethoxybenzyl, 2,4,6-trimethoxybenzyl and 4,4'-dimethoxybenzhydryl and the like.

Examples of carboxyl protecting groups are O- and S-esters (e.g., methyl, ethyl, t.butyl, benzyl, cyanomethyl, phthalimidomethyl, 4-picolyl, 2-p-tosylethyl, phenyl, p-nitrophenyl, thiophenyl and p-nitrobenzyl esters), amides or hydrazides (e.g. trityl, phenyl, carbobenzoxy and t.butoxycarbonyl hydrazides). Further, the carboxyl group can also be protected by salt formation.

In addition, the residue of a polymeric carrier can be considered as the amide protecting group or as the carboxyl protecting groups.

As special protecting groups for the histidine group there can be mentioned, for example, benzyl, p-nitrobenzyl, t.butoxycarbonyl, dinitrophenyl, trityl, benzyloxycarbonyl, adamantyloxycarbonyl, tosyl, piperidinocarbonyl and the like.

The manufacture of a radioiodinated phloretyl-β-alanyl-secretin in accordance with the process provided by the present invention is carried out by a conventional radioactive iodination of phloretyl-β-alanyl-secretin with $^{125}$I, $^{131}$I or $^{123}$I, with $^{125}$I being preferred.

Although the labelling technique which is used is not critical, there is preferably used the Chloramine T method described by Hunter and Greenwood in "Handbook of Experimental Immunology" or the lactoperoxidase method.

The method by which the purification of the radioactive material is carried out is not critical. However, this purification is advantageously carried out, after completion of the iodination process and binding of the degradation material on bovine serum albumin, via a cellulose column.

The radioiodinated phloretyl-β-alanyl-secretin provided by the present invention is a valuable reagent for the radioimmunological determination of secretin.

The present invention is also concerned with a method for the determination of secretin in a sample, which method comprises mixing said sample with a known amount of radioiodinated phloretyl-β-alanyl-secretin and an antibody specific for secretin, measuring the degree of binding of the labelled radioiodinated phloretyl-β-alanyl-secretin and determining the amount of secretin present in the sample by comparing the degree of binding with a standard curve which has been obtained by adding known amounts of secretin to a defined mixture of the radioiodinated phloretyl-β-alanyl-secretin and the antibody and determining the degree of binding for this known amount of secretin.

The phloretyl-β-alanyl-secretin used as the starting material as well as its salts or protected derivatives can be prepared in a manner which is customary in peptide chemistry.

Essentially, however, all preparative methods are based on the successive condensation of amino acids or protected polypeptides, the condensation being carried out in accordance with methods known per se.

For example, the condensation between the free amino group of one molecule and the free carboxyl group of another molecule can be carried out directly in the presence of a suitable condensation agent, such as, a carbodiimide selected from dicyclohexylcarbodiimide, 1-cyclohexyl-3-morpholinyl-carbodiimide and other condensation agents known from the literature. The condensation is advantageously carried out in the presence of dicyclohexylcarbodiimide with the addition of a 1,2-dinucleophile (e.g., N-hydroxysuccinimide and N-hydroxybenzotriazole) which suppresses racemization.

Further, the condensation can also be carried out via a suitable activated acyl derivative, such as, a mixed anhydride, azide, p-nitrophenyl ester, 2,4,5-trichlorophenyl ester and N-hydroxysuccinimide ester.

The condensations are conveniently carried out in an inert organic solvent, preferably in a polar organic solvent such as dimethylformamide, dimethyl sulphoxide, acetonitrile, a halogenated hydrocarbon such as dichloromethane, chloroform and the like. The condensation is conveniently also carried out at a temperature below room temperature.

The protecting groups are removed in a known manner such as by reduction with sodium in liquid ammonia, hydrogenation (e.g., in the presence of a palladium/charcoal catalyst), treatment with hydrogen halides (e.g., hydrogen bromide and hydrogen chloride) in acetic acid or treatment with trifluoroacetic acid, trifluoromethanesulphonic acid, boric acid-trifluoroacetic acid tris-anhydride, optionally with the addition of scavengers, such as, anisole and thiols.

For the preparation of a free amine from a salt thereof after a treatment with hydrogen halide in acetic acid, the hydrobromide, for example, is either treated with an ion exchanger or neutralized with an inorganic or organic base such as a tertiary amine (e.g., triethylamine).

The manner in which the resulting phloretyl-$\beta$-alanyl-secretin is purified is not critical. However, the purification is advantageously carried out by chromatography (e.g., on Sephadex) or by countercurrent distribution.

A preferred process for the preparation of phloretyl-$\beta$-alanyl-secretin is illustrated by the following Formula Scheme and the Examples hereinafter. The compounds of formulae II to VII, X to XIII and XV are novel and it will be appreciated that they also form part of the present invention.

Formula Scheme 1 illustrates the preparation of O-tert.-butyl-phloretyl-$\beta$-alanine and Formula Scheme 2 illustrates the preparation of phloretyl-$\beta$-alanyl-secretin.

In the Formulae Schemes and Examples there are used the following abbreviations and symbols which are customary in peptide chemistry:

Amino acid abbreviations formed from three letters which are usually the first three letters;

Phl: phloretyl;

Z: benzyloxycarbonyl (referred to, for example, by Bergmann et al in Berichte d. Dtsch. Chem. Ges., Vol 65, 1932, p. 1192 et seq.);

DCCD: dicyclohexylcarbodiimide procedure (referred to, for example, by Sheehan et al, J. Am. Chem. Soc., Vol 77, 1955, p. 1067 et seq.);

HOSU: N-hydroxysuccinimide;

DCCD/HOBT: dicyclohexylcarbodiimide/hydroxybenzotriazole procedure (reffered to, for example, by Koenig et al, Berichte d. Dtsch. Chem. Ges., Vol 103, 1970, p. 788 et seq.);

tBu: Tert.butyl;

TFA: trifluoroacetic acid;

AdOC: adamantylcarbonyl (referred to, for example, by Moroder et al, Symposium on Peptides and Proteins, Dushanbe (USSR), p. 36 (1976).

Formula Scheme 1

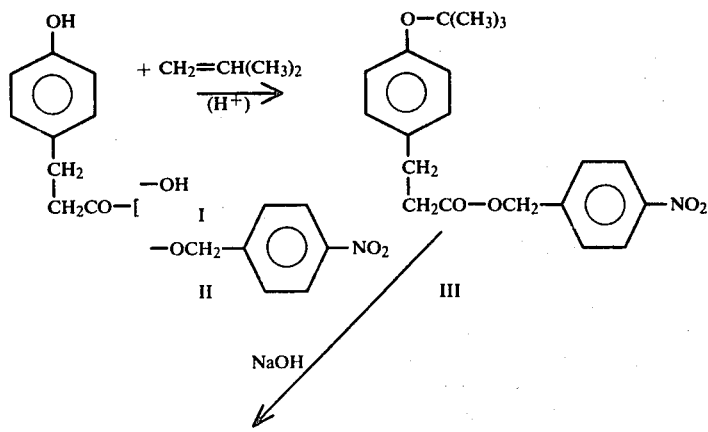

-continued
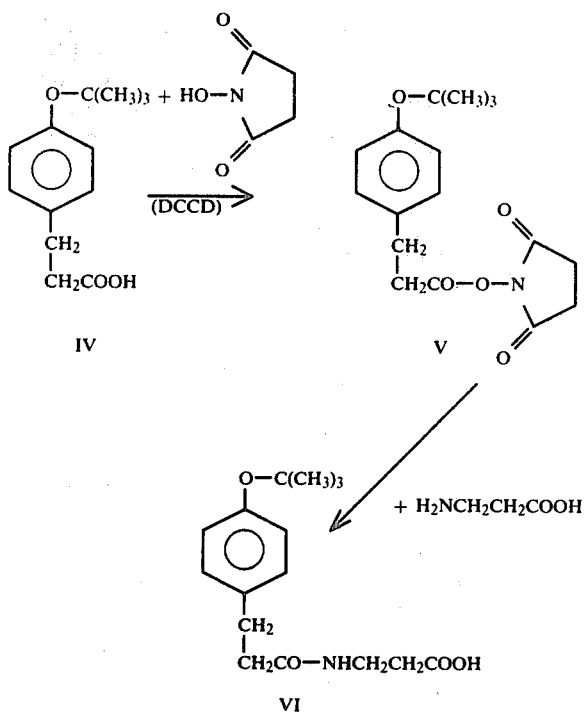
Formula Scheme 2
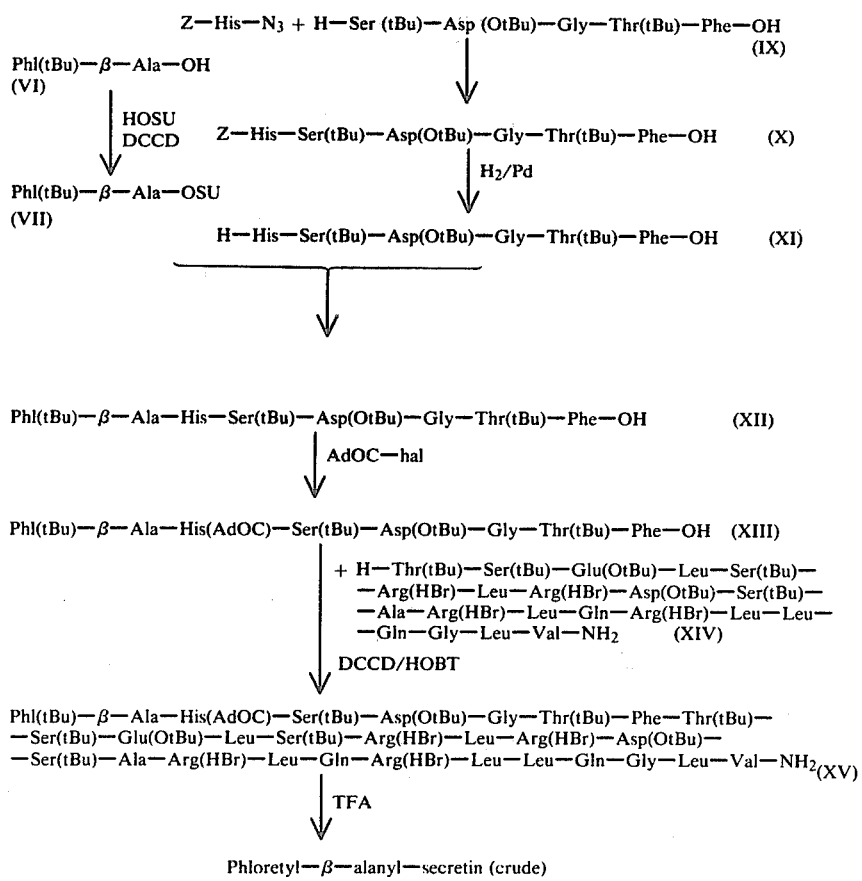
The following Examples illustrate the present invention:

Preparation of
3-(4-tert.butoxyphenyl)-propanoyl-β-alanine
[Phl(tBu)-β-Ala-OH]

2.48 g (28.0 mmol) of β-alanine in 100 ml of dimethylformamide/water (9:1) are treated at 0° C. with 3.9 ml (28.0 mmol) of triethylamine and 4.45 g (14.0 mmol) of 3-(4-tert.butoxyphenyl)-propionic acid N-hydroxysuccinimide ester [Phl(tBu)-OSU]. The mixture is stirred at 0° C. for 2 hours and then at room temperature for 12 hours, evaporated in vacuo and the residue partitioned between ethyl acetate and 1% potassium hydrogen sulphate solution. The organic phase is washed several times with 1% potassium hydrogen sulphate solution and water, dried over sodium sulphate and then evaporated in vacuo. The residue crystallizes from diisopropyl ether/petroleum ether. There is obtained 3-(4-tert.butoxyphenyl)-propanoyl-β-alanine of melting point 70°–72° C. The product is chromatographically pure in cyclohexane/chloroform/acetic acid (45:45:10) and n-heptane/tert.butanol/acetic acid (3:2:1). The yield amounts to 3.4 g (83% of theory).

The starting materials are prepared as follows:

(A) 3-(4-Hydroxyphenyl)-propionic acid 4-nitrobenzyl ester 1.66 g (10 mmol) of 3-(4-hydroxyphenyl)-propionic acid in 80 ml of dimethylformamide are treated at room temperature and while stirring with 2.16 g (10 mmol) of 4-nitrobenzyl bromide and 1.4 ml (10 mmol) of triethylamine. After 12 hours, the mixture is evaporated in vacuo and the residue obtained partitioned between ethyl acetate and water. The organic phase is separated, washed with 10% potassium hydrogen carbonate solution and water, dried over sodium sulphate and then evaporated to dryness. The residue crystallizes from diisopropyl ether/petroleum ether. There is obtained 3-(4-hydroxyphenyl)-propionic acid 4-nitrobenzyl ester in the form of colourless needles of melting point 80°–82° C. The product is chromatographically pure in cyclohexane/chloroform/acetic acid (45:45:10). The yield amounts to 1.6 g (53% of theory).

(B) 3-(4-Tert.butoxyphenyl)-propionic acid 4-nitrobenzyl ester 4.51 g (15 mmol) of 3-(4-hydroxyphenyl)-propionic acid 4-nitrobenzyl ester in 200 ml of methylene chloride are carefully treated at 0° C. with 100 ml of isobutene and 0.5 ml of concentrated sulphuric acid. The mixture is stored at room temperature for 72 hours and then poured into 100 ml of 0.4-N potassium hydrogen carbonate solution. The organic solvent is almost completely evaporated in vacuo and the product extracted several times with diethyl ether. The combined organic phases are washed with 0.5-N sodium hydroxide and water, dried over sodium sulphate and then evaporated. The solid residue is dissolved in petroleum ether, insoluble material is filtered off and the filtrate evaporated to dryness in vacuo. There is obtained 3-(4-tert.butoxyphenyl)-propionic acid 4-nitrobenzyl ester in the form of a crystalline residue of melting point 30°–32° C. The product is chromatographically pure in cyclohexane/chloroform/acetic acid (45:45:10). The yield amounts to 4.5 g (83% of theory).

(C) 4-(4-Tert.butoxyphenyl)-propionic acid 2.86 g (8 mmol) of 3-(4-tert.butoxyphenyl)-propionic acid 4-nitrobenzyl ester in 500 ml of dioxan are saponified while stirring with 8 ml of 2-N sodium hydroxide for 2 hours at 70° C. and for 12 hours at room temperature. After acidifying the solution with an equivalent amount of 1-N hydrochloric acid, the organic solvent is almost completely removed in vacuo and the residue partitioned between 40 ml of 0.5-N potassium hydrogen carbonate solution and diethyl ether. After cooling, the aqueous phase is cautiously acidified with 1-N hydrochloric acid and extracted several times with ethyl acetate. The combined organic phases are washed neutral with water, dried over sodium sulphate and evaporated in vacuo. A solution of the residue in heptane is filtered and evaporated to dryness in vacuo. There is obtained 3-(4-tert.butoxyphenyl)-propionic acid in the form of a crystalline residue of melting point 29°–31° C. The product is chromatographically pure in cyclohexane/chloroform/acetic acid (45:45:10). The yield amounts to 1.3 g (73% of theory).

(D) 3-(4-Tert.butoxyphenyl)-propionic acid N-hydroxysuccinimide ester [Phl(tBu)-OSU]

1.11 g (5.0 mmol) of 3-(4-tert.butoxyphenyl)-propionic acid and 0.58 g (5.0 mmol) of N-hydroxysuccinimide in 50 ml of ethyl acetate are treated at 0° C. with 1.03 g (5.0 mmol) of dicyclocarbodiimide. The mixture is stirred at 0° C. for 12 hours, filtered and the filtrate evaporated. The residue crystallizes from isopropanol. There is obtained 3-(4-tert.butoxyphenyl)-propionic acid N-hydroxysuccinimide ester of melting point 115°–116° C. The product is chromatographically pure in cyclohexane/chloroform/acetic acid (45:45:10) and in n-heptane/tert.butanol/acetic acid (3:2:1). The yield amounts to 1.3 g (81% of theory).

EXAMPLE 2

Preparation of 3-(4-tert.butoxyphenyl)-propanoyl-β-alanine N-hydroxysuccinimide ester To 3.5 g (11.9 mmol) of Phl(tBu)-β-Ala-OH in 60 ml of dimethylformamide are added at 0° C. 1.38 g (11.9 mmol) of N-hydroxysuccinimide and 2.47 g (11.9 mmol) of dicyclohexylcarbodiimide. The mixture is stirred at 0° C. for 12 hours, filtered and the filtrate evaporated in vacuo. The residue is crystallised twice from isopropanol. There is obtained 3-(4-tert.butoxyphenyl)-propanoyl-β-alanine N-hydroxysuccinimide ester of melting point 106°–107° C. The yield amounts to 2.9 g (63% of theory).

EXAMPLE 3

Preparation of
benzyloxycarbonyl-L-histidyl-O-tert.butyl-L-seryl-L-asparagyl(β-tert.butyl ester)-glycyl-O-tert.butyl-L-threonyl-L-phenylalanine monohydrate 1.02 ml (8.6 mmol) of tert.butyl nitrite are added at −15° C. while stirring to 2.37 g (7.8 mmol) of Z-His-NHNH$_2$ [melting point 164°–166° C. (recrystallized from methanol); $[\alpha]_D^{20} = -6.3°$ or $[\alpha]_{564}^{20} = -7.8°$ (c = 1 in dimethylformamide)] and 6.0 ml (31.2 mmol) of 5.9-N hydrogen chloride in dioxan in 60 ml of dimethylformamide. After 10 minutes, the solution is cooled to −50° C., neutralized with 4.37 ml (31.2 mmol) of triethylamine and treated with a solution, cooled to 0° C., of 4.75 g (6.5 mmol) of H-Ser(tBu)-Asp(OtBu)-Gly-Thr(tBu)-Phe-OH monohydrate and 0.715 ml (6.5 mmol) of N-methylmorpholine in 80 ml of dimethylformamide. The mixture is stirred at 0° C. for 12 hours and then at room temperature for a further 8 hours. The solvent is almost completely removed in vacuo and the residue partitioned between 200 ml of chloroform/n-butanol (9:1) and 130 ml of 1% potassium hydrogen sulphate solution. The organic phase is separated, washed sulphate-free with water, concentrated and poured into ethyl acetate. The precipitate obtained is filtered off and reprecipitated from methanol/ethyl acetate. There is obtained benzyloxycarbonyl-L-histidyl-O-tert.butyl-L-seryl-L-asparagyl($\beta$-tert.butyl ester)-glycyl-O-tert.butyl-L-threonyl-L-phenylalanine monohydrate of melting point 185°–189° C.; $[\alpha]_D^{20} = -3.7°$ or $[\alpha]_{546}^{20} = -4.7°$ (c=1.07 in methanol). The product is chromatographically pure in n-butanol/acetic acid/water (3:1:1). The yield amounts to 5.10 g (80% of theory).

EXAMPLE 4

Preparation of L-histidyl-O-tert.butyl-L-seryl-L-asparagyl-($\beta$-tert.butyl ester)-glycyl-O-tert.butyl-L-threonyl-L-phenylalanine monoacetate 4.3 g (4.37 mmol) of Z-His-Ser(tBu)-Asp(OtBu)-Gly-Thr(tBu)-Phe-OH monohydrate in 150 ml of 90% methanol and 1 ml of acetic acid are hydrogenated in the presence of palladium black as the catalyst. After completion of the hydrogenation, the filtrate is evaporated in vacuo and the residue reprecipitated from methanol/ethyl acetate/diethyl ether. There is obtained L-histidyl-O-tert.butyl-L-seryl-L-asparagyl($\beta$-tert.butyl ester)-glycyl-O-tert.butyl-L-threonyl-L-phenylalanine monoacetate of melting point 155°–158° C.; $[\alpha]_D^{20} = +21.4°$ or $[\alpha]_{546}^{20} = +25.3°$ (c=1.11 in methanol). The product is chromatographically pure in n-butanol/acetic acid/water (3:1:1) and in n-butanol/acetic acid/water/pyridine (60:6:24:20). The yield amounts to 3.2 g (82.5% of theory).

EXAMPLE 5

Preparation of 3-(4-tert.butoxyphenyl)-propanoyl-$\beta$-alanyl-L-histidyl-O-tert.butyl-L-seryl-L-asparagyl($\beta$-tert.butyl ester)-glycyl-O-tert.butyl-L-threonyl-L-phenylalanine 1.0 g (1.12 mmol) of H-His-Ser(tBu)-Asp(OtBu)-Gly-Thr(tBu)-Phe-OH monoacetate in 25 ml of dimethylformamide is treated successively while stirring with 0.32 ml (2.24 mmol) of triethylamine and 0.585 g (1.5 mmol) of Phl(tBu)-$\beta$-Ala-OSU. After a further 12 hours at room temperature, the solvent is evaporated and the residue partitioned between chloroform and 0.3 g of potassium hydrogen sulphate in water. The organic phase is separated, carefully washed sulphate-free with water and evaporated. The residue is suspended in n-butanol/ethyl acetate. The suspension is stirred at room temperature for 1 hour. The product is filtered off, washed with ethyl acetate and diethyl ether and dried in vacuo. There is obtained 3-(4-tert.butoxyphenyl)-propanoyl-$\beta$-alanyl-L-histidyl-O-tert.butyl-L-seryl-L-asparagyl($\beta$-tert.butyl ester)-glycyl-O-tert.butyl-L-threonyl-L-phenylalanine of melting point 117°–120° C.; $[\alpha]_D^{20} = +5.5°$ or $[\alpha]_{546}^{20} = +6.9°$ (c=1.05 in dimethylformamide). The product is chromatographically pure in n-butanol/acetic acid/water (3:1:1). The yield amounts to 1.21 g (98% of theory).

EXAMPLE 6

Preparation of 3-(4-tert.butoxyphenyl)-propanoyl-$\beta$-alanyl-N$^{im}$-adamantyloxycarbonyl-L-histidyl-O-tert.butyl-L-seryl-L-asparagyl($\beta$-tert.butyl ester)-glycyl-O-tert.butyl-L-threonyl-L-phenylalanine 1.0 g (0.09 mmol) of Phl(tBu)-$\beta$-Ala-His-Ser(tBu)-Asp(OtBu)-Gly-Thr(tBu)-Phe-OH in 35 ml of dimethylformamide is treated at 0° C. while stirring with 0.38 ml (2.7 mmol) of triethylamine and 0.36 g (1.8 mmol) of adamantyloxycarbonyl fluoride. The mixture is stirred at 0° C. for 12 hours and, after removal of the solvent in vacuo, the residue obtained is partitioned between chloroform and 1% potassium hydrogen sulphate solution. The organic phase is separated, washed sulphate-free with water, dried over sodium sulphate and then concentrated in vacuo. The product is precipitated with diethyl ether. There is obtained 3-(4-tert.butoxyphenyl)-propanoyl-$\beta$-alanyl-N$^{im}$-adamantyloxycarbonyl-L-histidyl-O-tert.butyl-L-seryl-L-asparagyl($\beta$-tert.butyl ester)-glycyl-O-tert.butyl-L-threonyl-L-phenylalanine of melting point 144°–145° C.; $[\alpha]_D^{20} = +17.8°$ or $[\alpha]_{546}^{20} = +21.3°$ (c=1.03 in methanol). The product is chromatographically pure in n-butanol/acetic acid/water (3:1:1). The yield amounts to 1.06 g (92% of theory).

EXAMPLE 7

Preparation of 3-(4-tert.butoxyphenyl)-propanoyl-$\beta$-alanyl-N$^{im}$-adamantyloxycarbonyl-L-histidyl-O-tert.butyl-L-seryl-L-asparagyl($\beta$-tert.butyl ester)-glycyl-O-tert.butyl-L-threonyl-L-phenylalanine-O-tert.butyl-L-threonyl-O-tert.butyl-L-seryl-L-glutamyl($\gamma$-tert.butyl ester)-L-leucyl-O-tert.butyl-L-seryl-L-arginyl(hydrobromide)-L-leucyl-L-arginyl(hydrobromide)-L-asparagyl($\beta$-tert.butyl ester)-O-tert.butyl-L-seryl-L-alanyl-L-arginyl(hydrobromide)-L-leucyl-L-glutaminyl-L-arginyl(hydrobromide)-L-leucyl-L-leucyl-L-glutaminyl-glycyl-L-leucyl-L-valinamide 0.683 g (0.53 mmol) of Phl(tBu)-$\beta$-Ala-His(AdOC)-Ser(tBu)-Asp(OtBu)-Gly-Thr(tBu)-Phe-OH and 0.55 g (0.175 mmol) of H-Thr(tBu)-Ser(tBu)-Glu(OtBu)-Leu-Ser(tBu)-Arg(HBr)-Leu-Arg(HBr)-Asp(OtBu)-Ser(tBu)-Ala-Arg(HBr)-Leu-Gln-Arg(HBr)-Leu-Leu-Gln-Gly-Leu-Val-NH$_2$ hydrobromide in 45 ml of dimethylformamide/dimethylacetamide/phosphoric acid tris-dimethylamide (2:6:3) is treated at $-15°$ C. with 0.24 ml (0.175 mmol) of triethylamine, 0.081 g (0.683 mmol) of 1-hydroxy-benzotriazole and 0.110 g (0.530 mmol) of dicyclohexylcarbodiimide. The mixture is stirred at 0° C. for 48 hours and, after the addition of 0.225 g (0.175 mmol) of Phl(tBu)-$\beta$-Ala-His(AdOC)-Ser(tBu)-Asp(OtBu)-Gly-Thr(tBu)-Phe-OH, 0.027 g (0.227 mmol) of 1-hydroxy-benzotriazole and 0.036 g (0.175 mmol) of dicylohexylcarbodiimide at $-15°$ C., at room temperature for a further 72 hours. After concentration of 20 ml in vacuo, the solution is poured into hot ethyl acetate. The separated precipitate is filtered off at room temperature and washed carefully with ethyl acetate. The product is suspended in water/methanol (3:1) and the resulting jelly is concentrated to a small volume after the addition of 10 ml of amyl alcohol. After the addition of ethyl acetate, the product is filtered off, washed with ether and rigorously dried. It is chromatographically uniform in n-butanol/acetic acid/water (3:1:1). The yield amounts to 0.66 g (87% of theory).

EXAMPLE 8

Preparation of 3-(4-hydroxyphenyl)-propanoyl-$\beta$-alanyl-L-histidyl-L-seryl-L-asparagyl-glycyl-L-threonyl-L-phenylalanyl-L-threonyl-L-seryl-L-glutamyl-L-leucyl-L-seryl-L-arginyl-L-leucyl-L-arginyl-L-asparagyl-L-seryl-L-alanyl-L-arginyl-L-leucyl-L-glutaminyl-L-arginyl-L-leucyl-L-leucyl-L-glutaminyl-glycy-L-leucyl-L-valinamide(Phlorityl-$\beta$-alanyl-secretin)

0.48 g (0.11 mmol) of Phl(tBu)-$\beta$-Ala-His(AdOC)-Ser(tBu)-Asp(OtBu)-Gly-Thr(tBu)-Phe-Thr(tBu)-Ser(tBu)-Glu(OtBu)-Leu-Ser-(tBu)-Arg(HBr)-Leu-Arg(HBr)-Asp(OtBu)-Ser(tBu)-Ala-Arg(HBr)-Leu-Gln-Arg(HBr)-Leu-Leu-Gln-Gly-Leu-Val-NH$_2$ is covered with 15 ml of anhydrous ice-cold trifluoroacetic acid and 1.0 ml of anisole. The clear solution which results after a short time is stirred at room temperature for 2.5 hours and subsequently evaporated in vacuo. The residue is dissolved in water and freeze-dried. The yield of crude product amounts to 0.43 g.

EXAMPLE 9

Purification of crude phloretyl-$\beta$-alanyl-secretin (crude DATA-secretin)

(i) Pre-purification by ion-exchange chromatography on SP-Sephadex (C-25):

Equilibrated ion-exchanger SP-Sephadex C-25 (ammonium form) is filled into a chromatography column of 30 cm length and 1 cm diameter as usual with starting buffer (0.02-N acetic acid adjusted to pH 6.0 with concentrated ammonia). A solution of 150 mg of "crude DATA-secretin" in 5 ml of 2-N acetic acid is introduced onto the column and eluted with the starting buffer at a flow rate of 23.5 g ml/hour. After the elution of 350 ml of eluate, the starting buffer is replaced by a second buffer (0.05-N acetic acid adjusted to pH 6.5 with concentrated ammonia) and, after elution of a further 600 ml of eluate, the second buffer is replaced by a third buffer (0.2-N acetic acid adjusted to pH 6.6 with concentrated ammonia), the elution with the second and third buffers being carried out at the same flow rate as the first buffer. The eluate is collected in portions of 25 ml each in the cells of a fraction collector (Serva-Linear II), the peptide distribution being ascertained by the continuous registration of the extinction of the solution at 206 and 254 nm (LKB-Uvicord III). Fractions 2–32 from the last buffer elution (a total of 775 ml) are lyophilized and there are obtained, after a further 2-fold lyophilization from 1% acetic acid (prior to the last lyophilizations filtration is carried out through a millipore filter MS; size GS; 0.22$\mu$ pore diameter), 93 mg (62% of theory) of pre-purified water-containing and acetate-containing DATA-secretin. By thin-layer chromatography on Kieselgel-60 ready-prepared plates (Merck) in n-butanol/acetic acid/water/pyridine (45:6:24:20) there are observed, in addition to the main component, some further impurities in small amounts.

(ii) Refining purification:

Method A: Partition chromatography on Sephadex G-25:

Ca 50 g of Sephadex G-25 (fine) are left to soak for several hours in the lower-phase of a two-phase system [prepared by mixing 1 liter of specially purified sec.-butanol (see E. Wünsch et al, Hoppe-Seyler's Z. Physiol. Chem., 353, 1716–1720), 1 liter of 0.05-N acetic acid and 50 ml of ethanol; pH of the lower phase: 3.4] and then filled into a column of 200 cm length and 1 cm diameter. After equilibration with ca 150 ml of upper phase, there is introduced onto the column a solution of 30 mg of the pre-purified DATA-secretin (see under I) in 2 ml of upper phase and elution is then carried out with upper phase at a flow rate of 13 ml/hour. The eluate is collected in portions of 3.25 ml each in the cells of a fraction collector (Serva Linear II), the peptide distribution being ascertained not only by continuous registration of the extinction of the solution at 254 nm (LKB-Uvicord I) but also by thin-layer chromatography. After combining fractions 33–39, the solvent is evaporated in vacuo, the residue dissolved in 5 ml of 1% acetic acid and the peptide material isolated by lyophilisation. After repeating the lyophilization twice from 1% acetic acid (filtration of the solution being previously carried out in each case through a millipore filter MS; see under I), there are obtained 12 mg of pure water-containing and acetate-containing DATA-secretin. A further 8 mg of the pure substance can be isolated by repeated re-chromatography of fractions 28–32 and 40–44 in an analogous manner. The total yield amounts to 67% of theory.

Method B: Continuous carrier-free electrophoresis:

Chamber electrolyte solution (0.022-N acetic acid adjusted to pH 6.9 with concentrated ammonia) is pumped through the separating chamber of a VaP$_2$ electrophoresis apparatus (Bender and Hobein, Munich; modified for fractionation in 95 receiving vessels) at a flow rate of 120 ml/hour. At a chamber voltage of 2400 volts (corresponding to a potential of 48 volts/cm) and a current of 105 milliamperes resulting from the given conditions, a solution of 20 mg of the pre-purified DATA-secretin (see under I) in 3 ml of chamber electrolyte is pumped through the dosage device over a period of 3 hours into the supply opening lying above receiving vessel No. 30. (Receiving vessel No. 1 lies at the anode side of the separation apparatus and receiving vessel No. 95 lies at the cathode side of the separation apparatus). After the input of the substance, the through-flow of the electrolyte solution is continued for ca 3 hours until the volume in each of the receiving vessels amounts to about 75 ml. The peptide distribution is ascertained by measuring the extinction at 220 nm. The substance (15 mg) isolated from fractions 32–43 by lyophilization is again subjected to electrophoresis under modified conditions (chamber electrolyte: 0.016-N acetic acid adjusted to pH 6.9 with concentrated ammonia; dosage 15 mg of substance in 3 ml of chamber electrolyte). By three-fold lyophilization (twice from 1% acetic acid after filtration through a millipore filter MS; see under I), there are isolated from fractions 32–43 10 mg of pure water-containing and acetate-containing DATA-secretin. By repeated re-electrophoresis of fractions 44–49 there are obtained a further 4 mg of pure substance. The total yield amounts to 70% of theory.

EXAMPLE 10

Preparation of phloretyl-$\beta$-alanyl-secretin ($^{125}$I-DATA-secretin)

1.25 $\mu$g of phloretyl-$\beta$-alanyl-secretin are reacted with 500 $\mu$ci of $^{125}$I in 0.3-M potassium phosphate buffer, pH 7.23, in the presence of 12.5 $\mu$g of Chloramine T. The iodination is terminated after 30 seconds by the addition of sodium sulphite. Degradation products are bound on 2.5% bovine serum albumin. The purification of the iodinated secretin derivative is carried out using a cellulose column. The yield of radioiodinated phloretyl-β-alanyl-secretin amounts of about 80% and the specific activity amounts to about 350 μci/ug.

EXAMPLE 11

Comparison of the immunoreactivity of iodinated secretin, iodinated 6-Tyr-secretin and iodinated DATA-secretin A) Material:

| | |
|---|---|
| Standard diluent: | 0.02-M Veronal buffer, pH 8.6, (Merck, Darmstadt) + 2% foetal bovine plasma (Flow Laboratories, England) + 5% Trasylol (Bayer, Leverkusen) |
| Total volume: | 2.5 ml. |
| Tracer: | $^{125}$I-DATA-secretin (prepared according to Example 10) $^{125}$I-secretin (prepared in an analogous manner to that described in Example 10 starting from secretin). $^{125}$I-6-Tyr-secretin (prepared in an analogous manner to that described in Example 10 starting from 6-Tyr-secretin (bought from Schwarz/Mann Division of Becton, Dickinson and Company, USA), activity used ca 1000 cpm. |
| Standard: | Natural secretin (GIH Research Unit, Karolinka Institute, Stockholm). |
| Albumen concentration | 2% foetal bovine plasma. |

(B) Method:

Various antibody sera A to E are tested. The antibody concentration is chosen so that the ratio of bound $^{125}$I-DATA-secretin to free $^{125}$I-DATA-secretin, namely the B/F ratio, after 80 hours incubation at 4° C. amounts to ca 1, i.e. 50% of the tracers used are bound.

The separation of the free antigen from the bound antigen is carried out by adding 0.5 ml of an active carbon suspension (25 mg/ml) at the end of the incubation period, mixing, centrifuging for 15 minutes at 3000 revolutions per minute, decanting and separately measuring the sediment and the supernatant.

By adding various amounts of secretin (0, 5, 10, 25, 50, 75, 100 and 125 pg/ml) there are determined standard curves, the values of which are given in Tables I to V hereinafter:

Table I

| | Antiserum A (dilution 1:150000) | | |
|---|---|---|---|
| Secretin (pg/ml) | $^{125}$I-DATA-secretin (B/F) | $^{125}$I-secretin (B/F) | $^{125}$I-6-Tyr-secretin (B/F) |
| 0 | 0.820 | 0.467 | 0.163 |
| 5 | 0.628 | 0.336 | 0.112 |
| 10 | 0.465 | 0.299 | 0.105 |
| 25 | 0.315 | 0.233 | 0.057 |
| 50 | 0.126 | 0.194 | 0.027 |
| 75 | 0.118 | 0.113 | 0.020 |
| 100 | 0.070 | 0.064 | 0.020 |
| 125 | 0.064 | 0.077 | 0.012 |

Table II

| | Antiserum B (dilution 1:250000) | | |
|---|---|---|---|
| Secretin (pg/ml) | $^{125}$I-DATA-secretin (B/F) | $^{125}$I-secretin (B/F) | $^{125}$I-6-Tyr-secretin (B/F) |
| 0 | 0.752 | 0.466 | 0.183 |
| 5 | 0.563 | 0.340 | 0.166 |
| 10 | 0.448 | 0.330 | 0.118 |
| 25 | 0.263 | 0.262 | 0.092 |
| 50 | 0.143 | 0.113 | 0.039 |
| 75 | 0.125 | 0.149 | 0.027 |
| 100 | 0.116 | 0.102 | 0.031 |
| 125 | 0.075 | 0.093 | 0.020 |

Table III

| | Antiserum C (dilution 1:2500000) | | |
|---|---|---|---|
| Secretin (pg/ml) | $^{125}$I-DATA-secretin (B/F) | $^{125}$I-secretin (B/F) | $^{125}$I-6-Tyr-secretin (B/F) |
| 0 | 1.000 | 0.824 | 0.356 |
| 5 | 0.953 | 0.830 | 0.326 |
| 10 | 0.755 | 0.793 | 0.318 |
| 25 | 0.520 | 0.340 | 0.184 |
| 50 | 0.299 | 0.317 | 0.137 |
| 75 | 0.212 | 0.196 | 0.088 |
| 100 | 0.134 | 0.139 | 0.092 |
| 125 | 0.103 | 0.117 | 0.044 |

Table IV

| | Antiserum D (dilution 1:2500000) | | |
|---|---|---|---|
| Secretin (pg/ml) | $^{125}$I-DATA-secretin (B/F) | $^{125}$I-secretin (B/F) | $^{125}$I-6-Tyr-secretin (B/F) |
| 0 | 1.210 | 0.650 | 0.275 |
| 5 | 0.811 | 0.466 | 0.226 |
| 10 | 0.543 | 0.383 | 0.116 |
| 25 | 0.280 | 0.208 | 0.081 |
| 50 | 0.116 | 0.090 | 0.031 |
| 75 | 0.081 | 0.084 | 0.023 |
| 100 | 0.047 | 0.090 | 0.016 |
| 125 | 0.041 | 0.010 | 0.010 |

Table V

| | Antiserum E (dilution 1:2500000) | | |
|---|---|---|---|
| Secretin (pg/ml) | $^{125}$I-DATA-secretin (B/F) | $^{125}$I-secretin (B/F) | $^{125}$I-6-Tyr-secretin (B/F) |
| 0 | 1.000 | 0.475 | 0.150 |
| 5 | 0.624 | 0.428 | 0.104 |
| 10 | 0.456 | 0.275 | 0.101 |
| 25 | 0.240 | 0.174 | 0.055 |
| 50 | 0.111 | 0.130 | 0.012 |
| 75 | 0.067 | 0.060 | 0.022 |
| 100 | 0.068 | 0.057 | 0.009 |
| 125 | 0.054 | 0.045 | 0.017 |

Tables I to V hereinbefore and the standard curves obtained therefrom show that $^{125}$I-DATA-secretin exhibits the strongest binding to the various secretin antibodies in comparison with $^{125}$I-secretin and $^{125}$I-6-Tyr-secretin; that is to say, $^{125}$I-DATA-secretin possesses the greatest immunoreactivity. The superiority of DATA-secretin as an iodinatable secretin derivative over the substances hitherto used for this purpose is accordingly unequivocally demonstrated.

I claim:

1. N-[3-(4-Hydroxy-3-$^{125}$I-phenyl)-propanoyl]-β-alanyl-secretin.

2. N-[3-(4-Hydroxy-3,5-di$^{125}$I-phenyl)-propanoyl]-β-alanyl-secretin.

3. Phloretyl-β-alanyl-secretin, a salt thereof or a protected derivative thereof.

* * * * *